United States Patent [19]

Nishiyama et al.

[11] 4,152,328

[45] May 1, 1979

[54] 2-PHENOXY-5-TRIFLUOROMETHYLPYRIDINE COMPOUNDS AND PROCESS FOR PREPARATION THEREOF

[75] Inventors: Ryuzo Nishiyama, Takatsuki; Kanichi Fujikawa; Takahiro Haga; Kuniaki Nagatani, all of Kusatsu, all of Japan

[73] Assignee: Ishihara Sangyo Kaisha Ltd., Osaka, Japan

[21] Appl. No.: 889,077

[22] Filed: Mar. 22, 1978

[30] Foreign Application Priority Data

Oct. 20, 1977 [JP] Japan .................................. 52-125065

[51] Int. Cl.² .............................................. C07D 213/64
[52] U.S. Cl. ........................................ 546/302; 71/94; 546/345
[58] Field of Search ................................. 260/297 R

[56] References Cited

U.S. PATENT DOCUMENTS 4,080,443   3/1978   Malhotra ..................... 260/294.8 K

*Primary Examiner*—John D. Randolph
*Attorney, Agent, or Firm*—Sughrue, Rothwell, Mion, Zinn and Macpeak

[57] ABSTRACT

A 2-phenoxy-5-trifluoromethylpyridine compound represented by the following general formula (I):

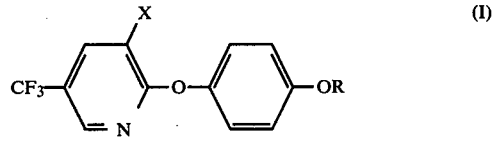

wherein X represents a hydrogen atom or a chlorine atom, and R represents a hydrogen atom or a cation, and a process for the preparation thereof.

8 Claims, No Drawings

2-PHENOXY-5-TRIFLUOROMETHYLPYRIDINE COMPOUNDS AND PROCESS FOR PREPARATION THEREOF

BACKGROUND OF THE INVENTION

1. Field of the Invention

This invention relates to novel 2-phenoxy-5-trifluoromethylpyridine compounds useful as intermediates in the preparation of medicines, agricultural chemicals, dyes, etc.

2. Description of the Prior Art

Hydroxy-substituted phenyl trifluoromethyl-substituted pyridyl ether compunds are described in German Patent Application (OLS) No. 2,700,019 with a general formula. However, no ether compounds in which a trifluoromethyl group is present at the 3- or 5-position of the pyridine ring of the moiety at all are specifically described in German Patent Application (OLS) No. 2,700,019.

SUMMARY OF THE INVENTION

The present invention provides a 2-phenoxy-5-trifluoromethylpyridine compound represented by the following general formula (I):

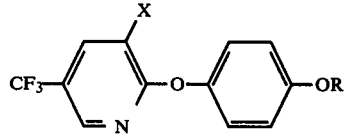

wherein X represents a hydrogen atom or a chlorine atom, and R represents a hydrogen atom or a cation.

The present invention also provides a process for preparing the compounds of the general formula (I).

DETAILED DESCRIPTION OF THE INVENTION

In the above-illustrated general formula (I), suitable cations for R include a sodium ion, a potassium ion, an ammonium ion, etc.

The 2-phenoxy-5-trifluoromethylpyridine compounds of the present invention represented by the general formula (I) can be prepared by reacting a compound represented by the general formula (II) with a compound represented by the general formula (III) to produce a pyridyloxyphenol compound represented by the general formula (IV) according to, for example, the following reaction scheme (1).

Reaction Scheme (1)

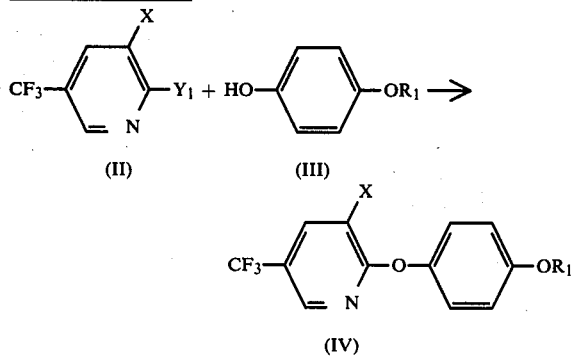

In the above reaction scheme (1), X is the same as defined in the general formula (I), $Y_1$ represents a fluorine atom or a chlorine atom, and $R_1$ represents a hydrogen atom or a ($C_1$–$C_5$) alkyl group.

The reaction is conducted at 70° to 200° C. for 1 to 12 hours in the presence of an alkaline material and a solvent. Where $R_1$ in the above reaction scheme (1) represents a hydrogen atom, i.e., where hydroquinone is used, the reaction is preferably conducted under an inert atmosphere, e.g., of nitrogen. A suitable solvent which can be used is a polar aprotic solvent such as dimethyl sulfoxide, dimethylformamide, hexamethylphosphoramide, sulfolane, etc., or a ketone solvent such as methyl ethyl ketone, methyl isobutyl ketone, etc., and a suitable alkaline material which can be used is an alkali metal hydroxide or an alkali metal carbonate such as sodium hydroxide, potassium hydroxide, sodium carbonate, potassium carbonate, etc.

Where $R_1$ is a ($C_1$–$C_5$) alkyl group, the alkyl group of the compound of the general formula (IV) can be removed using a known method of ether decomposition (dealkylation) to form a compound represented by the general formula (Ia):

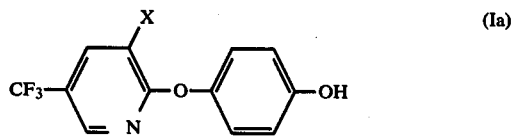

wherein X is the same as defined in the general formula (I).

The thus-obtained compound represented by the general formula (Ia) can be converted to a salt thereof represented by the general formula (Ib):

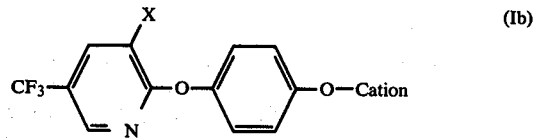

wherein X is the same as defined in the general formula (I), using conventional techniques by reacting an alkaline material therewith.

The starting material, the 2-substituted-5-trifluoromethylpyridine compound represented by the general formula (II), can be prepared by fluorinating a compound represented by the general formula (V) according to the following reaction scheme (1A).

Reaction Scheme (1A)

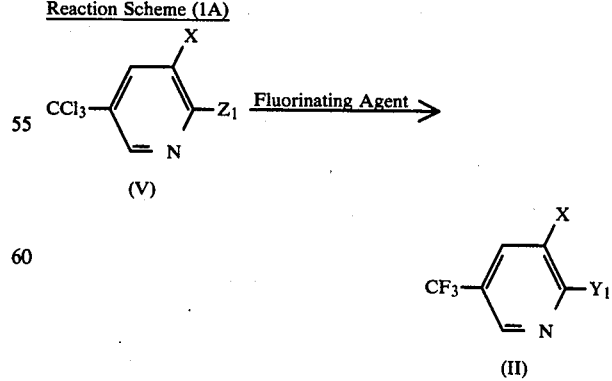

In the above reaction scheme (1A), X is as defined above for the general formula (I), $Y_1$ is the same as defined hereinbefore, and $Z_1$ represents a halogen atom with a fluorine atom, a chlorine atom and a bromine atom being preferred.

Where hydrogen fluoride is used as the fluorinating agent, the reaction is completed in 1 to 72 hours by treating the compound represented by the general formula (V) with gaseous hydrogen fluoride at 0° to 50° C. Upon conducting the reaction, an appropriate solvent may be used, if necessary.

Where metal fluorides such as antimony trifluoride are used as the fluorinating agent, the reaction is completed in 5 minutes to 1 hour by mixing the starting material, the compound represented by the general formula (V), with antimony trifluoride and heating the resulting mixture at 100° to 250° C. In addition, the end product, the 2-substituted-5-trifluoromethylpyridine compound represented by the general formula (II), can also be produced by heating and vaporizing the starting material, the 2-substituted-5-trichloromethylpyridine compound represented by the general formula (V), and reacting the vaporized starting material with a metal fluoride at an elevated temperature.

The compound represented by the general formula (V) can be produced by chlorinating, under ultraviolet light irradiation, a compound represented by the general formula (VI):

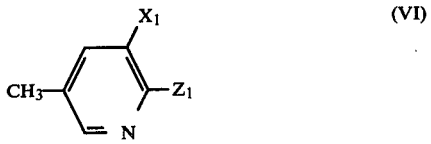

wherein $X_1$ represents a hydrogen atom, a chlorine atom or a bromine atom, and $Z_1$ is the same as defined hereinbefore, which can be produced by diazotizing 2-amino-5-methylpyridine with or without prior halogenation.

The 2-phenoxy-5-trifluoromethylpyridine compounds of the present invention represented by the general formula (I) can also be prepared by reacting a compound represented by the general formula (VII) with a compound represented by the general formula (VIII) to produce a compound represented by the general formula (Ia) according to the following reaction scheme (2).

Reaction Scheme (2)

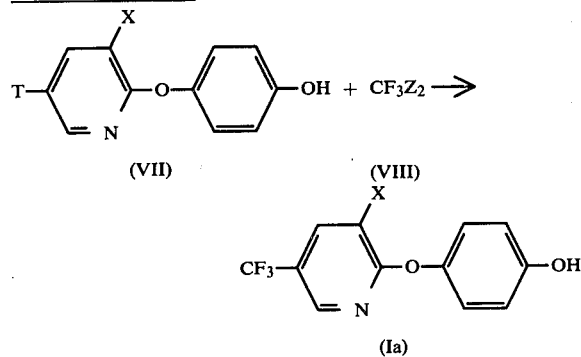

In the above reaction scheme (2), X is the same as defined in the general formula (I), and T and $Z_2$, which may be the same or different, each represents a bromine atom or an iodine atom.

The reaction is conducted for 5 to 24 hours at 100° to 200° C. in the presence of copper dust and a solvent, for example, a polar aprotic solvent such as pyridine, sulfolane, dimethylformamide, dimethyl sulfoxide, etc.

The starting materials described in the above methods are known in the art. For example, 2-amino-5-methylpyridine is described in Chemical Abstracts, Vol. b 43, 7050i (1949); the compounds of the general formulas (III) and (VII) are described in U.S. Pat. No. 4,046,553; and compounds of the general formula (VIII) are described in Org. Reaction, Vol. 9, P. 358.

The compounds of the present invention represented by the general formula (I) can be converted to the 4-(3-halogen substituted-5-trifluoromethylpyridyl-2-oxy)-phenoxyalkanecarboxylic acids, the 4-(5-trifluoromethylpyridyl-2-oxy)phenoxyalkanecarboxylic acids, the esters or the amides of these acids, etc., by reacting them with a halogen-substituted alkanecarboxylic acid, a halogen-substituted alkanecarboxylic acid ester or amide thereof, etc. These reactions can be conducted at 40° to 120° C. for 0.5 to 10 hours in the presence of an alkaline material. A suitable alkaline material which can be used is an alkali metal hydroxide or an alkali metal carbonate such as sodium hydroxide, potassium hydroxide, sodium carbonate, potassium carbonate, etc. In addition, the reactions may be conducted in the presence of a solvent such as methyl ethyl ketone, methyl isobutyl ketone, etc.

The above-described compounds produced from the compounds of the present invention represented by the general formula (I) show an excellent activity as active ingredients of, for example, agricultural chemicals, in particular, herbicides. Above all, selective herbicidal activity in withering gramineous weeds without substantial damage to crops in fields where broad-leaved crops such as cotton, soybeans, etc., are cultivated is noteworthy as a specific activity. Gramineous weeds which are selectively affected by these compounds produced from the compounds of the present invention represented by the general formula (I) include barnyard grass (Echinochloa crus-galli BEAUV.), large crabgrass (Digitaria adscendens HENR.), green foxtail (Setaria viridis BEAUV.), etc. The above-described compounds exhibit a distinct selective herbicidal activity on these gramineous weeds using either a pre-emergence soil treatment or a post-emergence foliage treatment. The degree of growth inhibition in the case of spraying, for example, 50 g per are (100 m²) as an active ingredient, was evaluated on a scale of 10 grades in which 10 indicates that growth was completely inhibited and 1 indicates no inhibition; the degree of growth inhibition of broad-leaved crops was 1 to 2, whereas the degree of growth inhibition of gramineous weeds was 9 to 10.

Representative examples of the preparation of the compounds of the present invention represented by the general formula (I) are described below. Unless otherwise indicated herein, all parts, percents, ratios and the like are by weight.

EXAMPLE 1

Preparation of 2-(4-Hydroxyphenoxy)-5-trifluoromethylpyridine

The starting material, 2-chloro-5-trifluoromethylpyridine, used in Preparation (A) and Preparation (B) below, was prepared according to the following process.

Preparation of 2-Chloro-5-trifluoromethylpyridine 23.1 g of 2-chloro-5-trichloromethylpyridine and 17.9 g of antimony trifluoride were mixed in a flask equipped with a thermometer, a stirrer and a reflux condenser. The reaction was initiated immediately when the mixture was heated to 170° C., and a formed low boiling product began to be refluxed. Five minutes after the initiation of the reflux, the condenser was directed downward to distill out the refluxing product. The distillate was extracted with methylene chloride, and the extract was washed successively with 15% dilute hydrochloric acid and water and, after drying over anhydrous sodium sulfate, the washed extract was concentrated. The concentrate was distilled to obtain 8.0 g of 2-chloro-5-trifluoromethylpyridine with a boiling point of 91°–93° C./80 mmHg.

Preparation (A)

40 ml of dimethyl sulfoxide, 4.2 g of hydroquinone, 5.0 g of 2-chloro-5-trifluoromethylpyridine and 2.3 g of potassium hydroxide were reacted at 150° C. for 2 hours with stirring in a nitrogen atmosphere. After the reaction product was allowed to cool, the product was added to a suitable amount of ice-water, neutralized with 30% concentrated hydrochloric acid, and extracted with methylene chloride. The extract was washed with water and dried over anhydrous sodium sulfate. 2.5 g of 2-(4-hydroxyphenoxy)-5-trifluoromethylpyridine (m.p. 82°–84° C.) was obtained by distilling off the methylene chloride.

Preparation (B)

40 ml of dimethyl sulfoxide, 5.0 g of hydroquinone monomethyl ether, 5.0 g of 2-chloro-5-trifluoromethylpyridine and 2.3 g of potassium hydroxide were reacted at 150° C. for 3 hours with stirring. After cooling, the reaction product was added to a suitable amount of ice-water, and extracted with methylene chloride. The extract was washed with water and dried over anhydrous sodium sulfate, followed by distilling off the methylene chloride. The residue containing 2-(4-methoxyphenoxy)-5-trifluoromethylpyridine was mixed with 5.0 g of pyridine hydrochloride and heated at 140°–160° C. for 2 hours with stirring. After cooling the system, the reaction product was added to a suitable amount of ice-water and extracted with methylene chloride. This methylene chloride layer was back-extracted with a 5% sodium hydroxide aqueous solution, and the extract was acidified with 30% concentrated hydrochloric acid to obtain a solid material. This solid material was filtered out and dried to obtain 2.1 g of 2-(4-hydroxyphenoxy)-5-trifluoromethylpyridine.

Preparation (C)

In an autoclave were placed 250 ml of pyridine containing dissolved therein 3.0 g of trifluorobromomethane, 7.3 g of 2-4-hydroxyphenoxy)-5-iodopyridine and 3.2 g of copper dust, and the reactants were reacted at 170° C. for 18 hours. After cooling the reaction system, pyridine was distilled off, and the residue was extracted with methylene chloride. The extract was washed successively with water and 15% dilute hydrochloric acid. After further washing with water, the extract was dried over anhydrous sodium sulfate. An oily material was obtained by distilling off the methylene chloride and was adsorbed on a silica gel column, then eluted with toluene to obtain 270 mg of 2-(4-hydroxyphenoxy)-5-trifluoromethylpyridine.

The thus-obtained 2-(4-hydroxyphenoxy)-5-trifluoromethylpyridine can be converted to ethyl α-[4-(5-trifluoromethylpyridyl-2-oxy)phenoxy]propionate using the following procedure.

5.1 g of 2-(4-hydroxyphenoxy)-5-trifluoromethylpyridine and 3.6 g of ethyl α-bromopropionate were dissolved in 50 ml of methyl ethyl ketone, and 3.3 g of anhydrous potassium carbonate was added thereto, followed by reacting for 2 hours under reflux (80° C.) conditions. Water was added to the reaction product to dissolve a solid material which formed. After concentrating under reduced pressure the solution to distill off the methyl ethyl ketone, the residue was extracted with toluene. The extract was washed with water and dried over anhydrous sodium carbonate, followed by distilling off the toluene to obtain an oily material. This oily material was solidified by cooling and then was washed with n-hexane and dried to obtain 1.8 g of ethyl α-[4-(5-trifluoromethylpyridyl-2-oxy)phenoxy]propionate (m.p. 63°–65° C.).

EXAMPLE 2

Preparation of the Sodium Salt of 4-(5-Trifluoromethylpyridyl-2-oxy)phenol 2.6 g of 2-(4-hydroxyphenoxy)-5-trifluoromethylpyridine prepared as described in Example 1 above was dissolved in 50 ml of ethanol, and 50 ml of ethanol containing 0.23 g of metallic sodium was added thereto. After stirring the mixture for a while, ethanol was distilled off to obtain 2.8 g of the title product.

EXAMPLE 3

Preparation of 2-(4-Hydroxyphenoxy)-3-chloro-5-trifluoromethylpyridine

The same procedures as described in Example 1, Preparation (A) were repeated except for using 6.0 g of 2,3-dichloro-5-trifluoromethylpyridine in place of 5.0 g of 2-chloro-5-trifluoromethylpyridine. After work-up, 2.6 g of the title product as a colorless semi-solid was obtained. This product was purified by being passed through a silica gel column. As a result, this product was solidified and found to have a melting point of 70° to 72° C.

EXAMPLE 4

Preparation of the Potassium Salt of 4-(3-Chloro-5-trifluoromethylpyridyl-2-oxy)phenol A solution prepared by adding 50 ml of ethanol to 0.56 g of potassium hydroxide previously dissolved in a small amount of water was mixed with a solution containing 2.9 g of 2-(4-hydroxyphenoxy)-3-chloro-5-trifluoromethylpyridine and 50 ml of ethanol and, after stirring the mixture for 10 minutes, ethanol was distilled off, followed by drying the resulting solid material to obtain 3.0 g of the title product.

While the invention has been described in detail and with reference to specific embodiments thereof, it will be apparent to one skilled in the art that various changes and modifications can be made therein without departing from the spirit and scope thereof.

What is claimed is:
1. A 2-phenoxy-5-trifluoromethylpyridine compound represented by the following general formula (I):

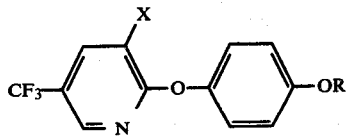 (I)

wherein X represents a hydrogen atom or a chlorine atom, and R represents a hydrogen atom or a cation.

2. The compound according to claim 1, wherein X represents a hydrogen atom.

3. The compound according to claim 1, wherein X represents a chlorine atom.

4. The compound according to claim 1, wherein said cation for R is a sodium ion, a potassium ion, or an ammonium ion.

5. 2-(4-Hydroxyphenoxy)-5-trifluoromethylpyridine, according to claim 1.

6. 4-(5-Trifluoromethylpyridyl-2-oxy)phenol sodium salt, according to claim 1.

7. 2-(4-Hydroxyphenoxy)-3-chloro-5-trifluoromethylpyridine, according to claim 1.

8. 4-(3-Chloro-5-trifluoromethylpyridyl-2-oxy)-phenol potassium salt, according to claim 1.

* * * * *